United States Patent

Maillard et al.

[11] 4,208,420
[45] Jun. 17, 1980

[54] NEW BENZO [d] THIAZOLE DERIVATIVES, PROCESS FOR THEIR PREPARATION AND THEIR THERAPEUTIC APPLICATIONS

[75] Inventors: Jacques Maillard, Versailles; Pierre Delaunay, Herblay; Jacky Legeai, Palaiseau, all of France

[73] Assignee: Laboratoires Jacques Logeais, Issy Les Moulineaux, France

[21] Appl. No.: 950,394

[22] Filed: Oct. 11, 1978

[30] Foreign Application Priority Data

Oct. 24, 1977 [FR] France .................... 77 31891

[51] Int. Cl.$^2$ ............ A61K 31/38; C07D 277/60
[52] U.S. Cl. .................... 424/270; 548/178
[58] Field of Search ........... 260/302 F; 424/270; 260/30 NR

[56] References Cited

U.S. PATENT DOCUMENTS 2,882,160  4/1959  De Stevens .............. 260/302 F

FOREIGN PATENT DOCUMENTS 497659  12/1938  United Kingdom .......... 260/302 F

OTHER PUBLICATIONS

Beilstein Handbuch Der Org. Chem., Band XXVII, 1st Suppl. Syst. No. 4341, p. 366 (1937).

*Primary Examiner*—Donald G. Daus
*Assistant Examiner*—D. B. Springer

*Attorney, Agent, or Firm*—Young & Thompson

[57] ABSTRACT

This invention relates to compounds having the general formula:

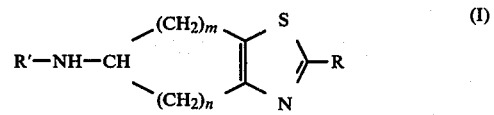

and their pharmaceutically acceptable acid addition salts having the formula:

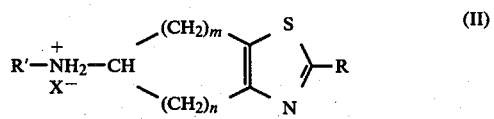

in which:
R represents hydrogen or a $C_{1-4}$ alkyl radical,
R' represents hydrogen or a $C_{1-4}$ alkyl radical,
m is 0, 1, 2 or 3,
n is 3, 2, 1 or 0,
the sum m+n being always equal to 3, and
X$^-$ represents an anion formed by a pharmaceutically acceptable acid.

Said compounds are typically useful as analgesic agents and as stimulants of the sympathetic nervous system, and also as central and peripheral vasoregulator agents.

5 Claims, No Drawings

NEW BENZO [d] THIAZOLE DERIVATIVES, PROCESS FOR THEIR PREPARATION AND THEIR THERAPEUTIC APPLICATIONS

This invention relates to new benzo[d]thiazole derivatives, to a process for their preparation and to their therapeutic applications.

This invention relates to compounds having the general formula:

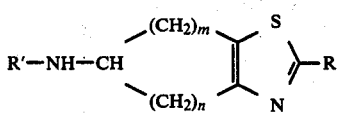

and their pharmaceutically acceptable acid addition salts having the formula:

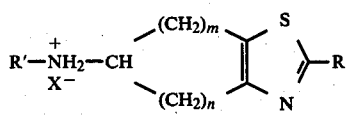

in which:
R represents hydrogen or a $C_{1-4}$ alkyl radical,
R' represents hydrogen or a $C_{1-4}$ alkyl radical,
m is 0, 1, 2 or 3,
n is 3, 2, 1 or 0,
the sum m+n being always equal to 3, and
$X^-$ represents an anion formed by a pharmaceutically acceptable acid.

The addition salts may typically be those formed with hydrochloric, hydrobromic and sulfuric acids and the pharmaceutically acceptable organic acids.

The compounds of the formula (I) may be obtained in the following manner, comprising:

(a) reacting a halogenated keto-ester of the formula:

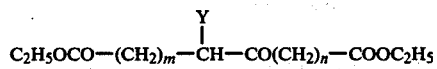

in which m and n are as defined above and Y is halogen, with a thioamide having the formula:

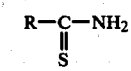

in which R has the above-defined meaning, within a solvent, typically an alcohol such as ethanol, in the presence or the absence of pyridine, to give a thiazole having the formula:

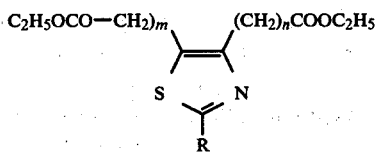

(b) cyclizing the thiazole of the formula (V) to give a keto-ester having the formula:

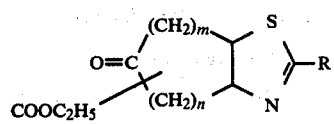

in the presence of an alkali metal alkoxide such as sodium ethoxide, within an ether or a saturated or aromatic hydrocarbon, such as benzene, according to the usual Dieckmann cyclization conditions.

(c) hydrolyzing compound (VI) in the hot, in aqueous or aqueous-alcoholic acidic medium, to give, with simultaneous decarboxylation, a ketone having the formula:

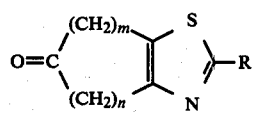

(d) reacting the resulting ketone of the formula (VII) with an amine having the formula $R'-NH_2$ in which R' is as previously defined, and hydrogenating the resulting imine, having the formula:

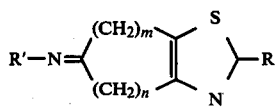

in which R, R', m and n are as previously defined, to give a compound of the formula (I).

The two steps of stage (d) may be carried out simultaneously or in succession. Thus, amine $R'NH_2$ may be reacted under pressure, in a hydrogen atmosphere, at room temperature or in the hot, in the presence of a catalyst such as Raney Nickel and within a solvent such as an alcohol. It is also possible to react only the amine of the formula $R'NH_2$ in alcohol solution, to isolate the resulting imine of the formula (VIII) and to hydrogenate the imine in the presence of a catalyst such as Raney nickel, platinum-over-charcoal or platinum oxide.

A number of compounds of the formula (III) are known. The compounds of the formula (III) in which m=0, 1 or 3 may be obtained by direct halogenation within a solvent inert with respect to the halogen chosen (chlorine, or preferably bromine) of a keto-ester having the formula:

The compounds of the formula (III) in which m=2 may be obtained by action of a halogenated derivative of the formula:

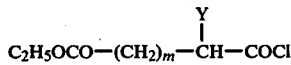

with sodium ethyl acetoacetate or sodium ethyl malonate, followed by hydrolysis to remove the group $-COCH_3$ or $-COOC_2H_5$.

The compounds of the formula (II) are obtained in the usual manner, by action of an acid on a compound of the formula (I), within a suitable solvent.

The following Examples illustrate the preparation of compounds of the formulae (I) and (II).

EXAMPLE 1

(a) Ethyl 3-bromo-4-oxo-pimelate (III; m=1; n=2)

Ethyl 4-oxo-pimelate (115 g; 0.5 mole) is dissolved in ethyl ether (150 ml) and bromine (80 g; 0.5 mole) is added thereto, with stirring. After reaction of the bromine is complete, the solution is concentrated under reduced pressure, and then the residue is washed to neutrality, dried in vacuo and used crude for the subsequent reactions.

(b) 2-Methyl-5-ethoxycarbonylmethyl-4-(2-ethoxycarbonylethyl)-thiazole (V; m=1; n=2; R=CH₃)

The crude product obtained in step (a) is dissolved in anhydrous ethanol (150 ml) with thioacetamide (37.5 g; 0.5 mole). The mixture is stirred for 70 hours at room temperature, after which the ethanol is distilled off and the residue is taken up into water and ethyl ether. The ether phase is repeatedly extracted with 2 N sulfuric acid, and is then combined with the aqueous phase. The latter is adjusted to pH 7: the oil which separates is extracted with ether and distilled under reduced pressure: $b.p._{0.2}=135°-140°$ C.; Weight: 78.5 g. Overall yield: 54%.

(c) 2-Methyl-7-ethoxycarbonyl-6-oxo-4,5,6,7-tetrahydrobenzo[d]thiazole (VI; m=1; n=2; R=CH₃)

A fresh solution of sodium ethoxide in ethyl ether is prepared by dissolving 5.7 g (0.248 g-at.) sodium in 200 ml anhydrous ethanol, evaporating off the alcohol and taking up the resulting material into 200 ml anhydrous ether. 70.5 g (0.248 mole) of the product obtained in step (b) is then added thereto. After stirring for 40 hours at room temperature, acetic acid (15 g; 0.250 mole) is added, the material is then evaporated to dryness and the residue is taken up into water and ethyl acetate. The organic phase is separated and distilled; the residue is distilled under reduced pressure: $b.p._{0.3}=135°-140°$ C. (with slight decomposition). Yield: 95%.

The position of the ethoxycarbonyl grouping could, a priori, occur either on carbon 7 (Formula A) or on carbon 5 (Formula B), according to the direction of Dieckmann's cyclization. This ambiguity was resolved by the NMR spectrum which shows the absence of coupling with the isolated proton situated on the carbon which carries group COOC₂H₅, which is consistent only with Formula A:

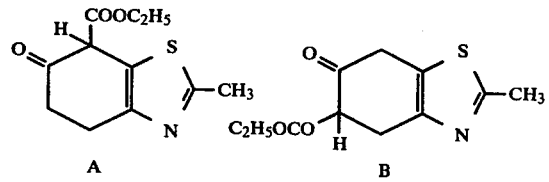

(d) 2-Methyl-6-oxo-4,5,6,7-tetrahydro-benzo[d]thiazole (VII; m=1; n=2; R=CH₃)

A mixture of 10 g (0.042 mole) of the keto-ester obtained in step (c) and 100 ml N hydrochloric acid is refluxed during 24 hours. After decolorization with charcoal, the solution is adjusted to pH 5 and repeatedly extracted with ethyl acetate. Evaporation of the solvent gives 6 g (86%) oil which crystallizes. M.p.=95°-96° C.

(e) 2-Methyl-6-amino-4,5,6,7-tetrahydro-benzo[d]thiazole hydrochloride (II; m=1; n=2; R=CH₃; R'=H; X=Cl)

9 g (0.054 mole) of the product obtained in step (d) are dissolved in 200 ml ethanol and introduced into an autoclave with 20 g ammonia and 5 g Raney nickel. The autoclave is filled with hydrogen, under a total pressure of 55 bars, and is heated at 100° C. for 2 hours. After cooling, the catalyst is filtered off and the alcohol is evaporated off and the residual oil is fractionated: $b.p._{0.5}=110°-130°$ C.

The base is purified as the carbonate, by bubbling a stream of CO₂ through an ethereal solution. The carbonate which precipitates is suction filtered, washed with ether and dried in vacuo. Base (V) is recovered by heating at 100° C. under 15 mm Hg. $B.p._{0.5}=120°-130°$ C.

In view of its oxidizability, it is immediately converted to the hydrochloride, by addition of a slight deficiency of anhydrous hydrochloric acid, in ethereal solution. M.p.=225° C. (dec.) Overall Yield: 67%.

EXAMPLE 2

2-Methyl-6-methylamino-4,5,6,7-benzo[d]thiazole (I; m=1; n=2; R=R'=CH₃)

To 10 g (0.062 mole) of the product obtained in step (d) of Example 1, dissolved in 200 ml ethanol, are added 20 g methylamine and 5 g Raney nickel, and the resulting material is hydrogenated in an autoclave under a pressure of 55 bars, under the same conditions as in Example I(e). The base is obtained, on evaporation of the solvent, in a yield of 72%. $B.p._{0.1}=86°-88°$ C.

The base is quantitatively converted to the hydrochloride, with anhydrous HCl in ethereal solution (II; m=1; n=2; R=R'=CH₃; X=Cl). M.p.=260° C. (dec.).

EXAMPLE 3

(a) 5-Ethoxycarbonylmethyl-4-(2-ethoxycarbonyl)-ethyl)-thiazole (V; m=1; n=2; R=H)

Ethyl 3-bromo-4-oxo-pimelate (212.5 g; 0.68 mole; obtained in step (a) of Example 1) is dissolved in anhydrous ethanol (380 ml) and freshly prepared thioformamide (41.6 g; 0.68 mole) is added thereto. After the initially exothermic reaction, the mixture is maintained for 20 hrs at room temperature. The ethanol is evaporated under reduced pressure and the residue is taken up into ether. The ether-insoluble hydrobromide of the resulting product is suction filtered, dissolved in a minimum amount of water and adjusted to pH 6 with a saturated aqueous sodium bicarbonate solution. The base is extracted with ethyl acetate, washed with water, dried and distilled under reduced pressure, to give 84 g (45%) of product, $b.p._{0.5}=139°-148°$ C.

(b) 7-Ethoxycarbonyl-6-oxo-4,5,6,7-tetrahydro-benzo[d]thiazole (VI; m=1; n=2; R=H)

This compound is prepared from the product obtained in step (a), using the procedure described in Example 1(c). The product, which crystallizes, is recrystallized from isopropyl oxide. M.p.=47°–50° C.; Yield: 72%.

(c) 6-Oxo-4,5,6,7-tetrahydro-benzo[d]thiazole (VII; m=1; n=2; R=H)

This compound is prepared by hydrolysis and decarboxylation of the keto-ester obtained in step (b), according to the procedure described in Example 1(d). Yield: 85% (the product has poor stability in air).

(d) 6-Methylamino-4,5,6,7-tetrahydro-benzo[d]thiazole hydrochloride (II; m=1; n=2; R=H; R'=CH$_3$; X=Cl)

This compound is prepared by action of methylamine, in the presence of hydrogen and Raney nickel, on the ketone obtained in step (c), according to the procedure described in Example 1(e). The base of the formula (I) is distilled under reduced pressure. E$_{0.5}$=88°–90° C.

The hydrochloride is formed by addition of a slight deficiency of anhydrous hydrochloric acid in ethyl ether solution. M.p.=224°–225° C. Yield: 75%.

EXAMPLE 4

(a) Ethyl 3-bromo-2-oxo-pimelate (III; m=3; n=0)

11 g (0.043 mole) ethyl 2-oxo-pimelate are brominated by addition of 6.9 g (0.043 mole) bromine in ether, as described in Example 1(a).

(b) 4-Ethoxycarbonyl-5-(3-ethoxycarbonyl-propyl)-thiazole (V; m=3; n=0; R=H)

The product is prepared from ethyl 3-bromo-2-oxo-pimelate, using the procedure described in Example 3(a); b.p.$_{0.6}$=158°–170° C. Yield: 58%

(c) 5-Carbethoxy-4-oxo-4,5,6,7-tetrahydro-benzo[d]-thiazole (VI; m=3; n=0; R=H)

This compound is prepared from the product obtained in step (b), by cyclization with sodium ethoxide, according to the procedure of Example 1(c). The desired product crystallizes from isopropyl oxide. M.p.=81°–82° C. Yield: 67%.

(d) 4-Oxo-4,5,6,7-tetrahydro-benzo[d]thiazole (VII; m=3; n=0; R=H)

This compound is obtained by acid hydrolysis and decarboxylation of the keto-ester obtained in step (c), according to the procedure of Example 1(d). It is crystallized from isopropyl oxide. M.p.=121°–122° C. Yield: 59%

(e) 4-Methylimino-4,5,6,7-tetrahydro-benzo[d]thiazole (VIII; m=3; n=0; R=H; R'=CH$_3$)

6 g (0.039 mole) of the ketone obtained in step (d) are dissolved in 50 ml anhydrous ethanol and treated for 30 minutes with a gaseous methylamine stream. After evaporation to dryness, the residue is taken up into ether and filtered, to give 5.6 g (86%) of product, M.p. 233°–235° C.

(f) 4-Methylamino-4,5,6,7-tetrahydro-benzo[d]thiazole (I; m=3; n=0; R=H; R'=CH$_3$)

Catalytic hydrogenation of the 4-methylimino derivative obtained in step (e) in ethanol containing excess methylamine, in the presence of platinum oxide, proceeds slowly at 50° C. under ordinary pressure. After the theoretical amount of hydrogen has been taken up, the solution is filtered, evaporated, and the residue is distilled: B.p.$_{0.4}$=86°–88° C.; Yield; 80%.

EXAMPLE 5

(a) 2-Methyl-4-ethoxycarbonyl-5-(3-ethoxycarbonyl-propyl)-thiazole (V; m=3; n=0; R=CH$_3$)

This compound is prepared from ethyl 3-bromo-2-oxo-pimelate (described in Example 4(a)), according to the procedure of Example 1(b). B.p.$_{0.3}$=150°–160° C. Yield: 57%.

(b) 2-Methyl-4-oxo-4,5,6,7-tetrahydro-benzo[d]thiazole (VII; m=3; n=0; R=CH$_3$)

The compound is prepared from the product obtained in step (a), by cyclization with sodium ethoxide, followed by hydrolysis and decarboxylation of the crude ester. B.p.$_{0.2}$=130°–140° C. M.p.=86°–87° C. Overall yield: 26%.

(c) 2-Methyl-4-amino-4,5,6,7-tetrahydro-benzo[d]thiazole hydrochloride (II; m=3; n=0; R=CH$_3$; R'=H; X=Cl)

The compound is prepared from the product obtained in step (b), according to the procedure described in Example I(e). M.p.=144°–146° C.

EXAMPLE 6

(a) 2-Methyl-7-oxo-4,5,6,7-tetrahydro-benzo[d]thiazole (VII; m=0; n=3; R=CH$_3$)

The compound is prepared according to a procedure identical with that of Example 5(b). B.p.$_{0.5}$=96°–100° C. Yield: 41%.

(b) 2-Methyl-7-methylimino-4,5,6,7-tetrahydro-benzo[d]-thiazole (VIII; m=0; n=3; R=R'=CH$_3$)

The compound is obtained by action of methylamine in ethanol, at 100° C. After distillation of the ethanol, the residue is taken up into ether and crystallized after evaporation of the latter. M.p.=65° C. (dec.). Yield: 84%.

(c) 2-Methyl-7-methylamino-4,5,6,7-tetrahydro-benzo[d]-thiazole (I, m=0; n=3; R=R'=CH$_3$)

The compound is obtained by catalytic hydrogenation of the methylimine obtained in step (b) in ethanol, at 100° C., and under a pressure of 100 bars, in the presence of 5% platinum-over-charcoal. B.p.$_{0.1}$=100°–110° C. Yield: 58%.

EXAMPLE 7

5-Amino-4,5,6,7-tetrahydro-benzo[d]thiazole (I; m=2; n=1; R=R'=H)

The compound is prepared by action of ammonia, in the presence of hydrogen and of Raney nickel, on corresponding ketone VII, according to the procedure described in Example 1(e).

B.p.$_{0.4}$=80°–84° C.; Hydrochloride: M.p.=213°–214° C.

The characteristics of the compounds of the formula (I) and of their salts of the formula (II) are tabulated in following Tables I and II, respectively, together with those of other compounds of the formulae (I) and (II) obtained in an analogous manner.

TABLE I

| Ex. | m | n | R | R' | Yield % | Physical constants (°C.) |
|---|---|---|---|---|---|---|
| 1 | 1 | 2 | CH$_3$ | H | 67 | B.p.$_{0.5}$ : 120–130 |
| 2 | 1 | 2 | CH$_3$ | CH$_3$ | 72 | B.p.$_{0.1}$ : 86–88 |
| 3 | 1 | 2 | H | CH$_3$ | 37 | B.p.$_{0.5}$ : 88–90 |
| 4 | 3 | 0 | H | CH$_3$ | 80 | B.p.$_{0.4}$ : 86–88 |
| 5 | 3 | 0 | CH$_3$ | H | 60 | B.p.$_{0.4}$ : 72–76 |
| 6 | 0 | 3 | CH$_3$ | CH$_3$ | 58 | B.p.$_1$ : 100–110 |
| 7 | 2 | 1 | H | H | 48 | B.p.$_{0.4}$ : 80–84 |
| 8 | 3 | 0 | CH$_3$ | CH$_3$ | 91 | B.p.$_{0.4}$ : 80–90 |
| 9 | 3 | 0 | H | H | 35 | B.p.$_{0.4}$ : 70–74 |
| 10 | 2 | 1 | CH$_3$ | H | 56 | B.p.$_{1.5}$ : 120–124 |
| 11 | 1 | 2 | H | H | 18 | B.p.$_{0.6}$ : 120–130 |
| 12 | 1 | 2 | H | n-C$_4$H$_9$ | 52 | B.p.$_{0.01}$ : 103–105 |
| 13 | 1 | 2 | CH$_3$ | iC$_3$H$_7$ | 10 | B.p.$_{0.05}$ : 79–80 |
| 14 | 1 | 2 | nC$_3$H$_7$ | CH$_3$ | 45 | B.p.$_{0.25}$ : 109–110 |
| 15 | 1 | 2 | iC$_3$H$_7$ | CH$_3$ | 56 | B.p.$_{0.4}$ : 107–109 |
| 16 | 1 | 2 | nC$_4$H$_9$ | CH$_3$ | 58 | B.p.$_{0.15}$ : 118–120 |

TABLE II

| Ex. | m | n | R | R' | X | Yield % | M.P. (°C.) |
|---|---|---|---|---|---|---|---|
| 1 | 1 | 2 | CH$_3$ | H | Cl | — | 255 (dec.) |
| 2 | 1 | 2 | CH$_3$ | CH$_3$ | Cl | 100 | 260 (dec.) |
| 3 | 1 | 2 | H | CH$_3$ | Cl | 75 | 224–225 |
| 4 | 3 | 0 | H | CH$_3$ | Cl | 93 | 216–218 |
| 5 | 3 | 0 | CH$_3$ | H | Cl | 83 | 144–146 |
| 6 | 0 | 3 | CH$_3$ | CH$_3$ | Cl | 74 | 176–177 |
| 7 | 2 | 1 | H | H | Cl | 85 | 213–215 |
| 8 | 3 | 0 | CH$_3$ | CH$_3$ | Cl | 90 | 233–235 |
| 9 | 3 | 0 | H | H | Cl | 100 | 230 (subl) |
| 10 | 2 | 1 | CH$_3$ | H | Cl | 100 | 226–228 |
| 11 | 1 | 2 | H | H | Cl | 65 | 335 (dec.) |
| 12 | 1 | 2 | H | n-C$_4$H$_9$ | Cl | 100 | >250 (subl) |
| 14 | 1 | 2 | nC$_3$H$_7$ | CH$_3$ | Cl | 99 | 245 |
| 15 | 1 | 2 | iC$_3$H$_7$ | CH$_3$ | Cl | 90 | 245 (dec.) |
| 16 | 1 | 2 | nC$_4$H$_9$ | CH$_3$ | Cl | 98 | 235 |

The compounds of the formula (I) and their salts of the formula (II) possess useful pharmacological properties, generally related to an interaction with the amines of the sympathetic nervous system, particularly with dopamine. Thus, they exhibit hypertensive, or hypotensive, anorexiant, analgesic and anti-inflammatory properties, and also stimulant or sedative properties on the sympathetic nervous system, at the central or peripheral level, as the case may be.

The tests used to demonstrate said properties are the conventionally used tests:

(1) for the central nervous system:
determination of the spontaneous motor activity, in mice;
potentiation of nembutal-induced sleep, in mice;
potentiation of d-amphetamine-induced stereotypes, in rats;
antagonism of reserpine-induced palpebral ptosis, in rats;

(2) for analgesy;
antagonism to the pain contractions subsequent to intraperitoneal injection of 0.75% acetic acid, in mice (Koster test)
inhibition of pain, in mice placed on a heating plate (Eddy test)

(3) for inflammation:
inhibition of edema of the paw on subcutaneous carrageenin injection, in rats;

(4) for the cardiovascular system:
determination of the blood pressure, of the femoral rate of flow and of the heart rate, and research for an antagonism or a potentiation of the catecholamines (epinephrine norepinephrine) on said parameters, in dogs;
research of an action on the unstriated fibers of the isolated saphena vein in dogs, and of the isolated ear artery of rabbits, in vitro.

The test materials were administered as the hydrochlorides, either intraperitoneally (or intravenously, in the course of cardiovascular tests), or orally.

The test materials exhibit generally, at varying degrees:
a central stimulant effect (increase of spontaneous motility, of amphetamine-induced stereotypes; of the antagonism of reserpine), sometimes accompanied by an anorexiant effect (decreased food intake, in rats);
an analgesic effect, which is sometimes quite substantial, together with an anti-inflammatory action;
a biphasic cardiovascular action, characterized by hypotension and vasodilation at low dosages, and by a hypertension which originates from a vasoconstriction observable both in vitro and in vivo, at high dosages.

Considered together, said activities approximate those observed with the catecholamines, and particularly with the dopaminergic stimulants.

The results obtained with some of the compounds are given in Table III for illustrative purposes.

In addition to the results set forth in Table III, the compound of Example 3 has a marked cerebral protecting effect against hypoxic asphyxia under a reduced oxygen pressure.

On the other hand, the same product has a potent inhibiting effect on the development of gastric ulcers due to stress, in rats.

Acute toxicity, in mice, is low, both intraperitoneally and orally.

TABLE IV

| Compound of | Acute toxicity, LD$_{50}$ mg/kg | |
|---|---|---|
| Example: | i.p. | p.o. |
| 1 | <100 | >200 |
| 2 | ≧100 | >200 |
| 3 | >200 | >200 |
| 4 | >200 | >200 |
| 7 | >200 | >200 |

TABLE III

| Compound of Example No. | Action on the central nervous system (administration p.o.) | Analgesic action | | Anti-inflammatory action ED$_{50}$ p.o. (mg/kg) | Cardiovascular action (i.v. administration) |
|---|---|---|---|---|---|
| | | Koster test ED$_{50}$ p.o. mg/kg | Eddy test ED$_{50}$ p.o. mg/kg | | |
| 1 | Inhibition of reserpine-induced ptosis at 10 mg/kg (40%) | — | — | 30 | Hypotension at 0.5 mg/kg Hypertension at 1–5 mg/kg Contraction of isolated veins and arteries at 2 × 10$^{-6}$ g/ml |

TABLE III-continued

| Compound of Example No. | Action on the central nervous system (administration p.o.) | Analgesic action | | Anti-inflammatory action ED$_{50}$ p.o. (mg/kg) | Cardiovascular action (i.v. administration) |
|---|---|---|---|---|---|
| | | Koster test ED$_{50}$ p.o. mg/kg | Eddy test ED$_{50}$ p.o. mg/kg | | |
| 2 | Increase of amphetamine-induced stereotypes, and anorexiant action at 3 mg/kg | 30 | 3 | $\leq 10$ | Hypotension at 0.5 mg/kg<br><br>Hypertension at 1 mg/kg, with increase of the femoral rate of flow<br>Contraction of isolated veins and arteries at $2 \times 10^{-6}$ g/ml |
| 3 | Increase of spontaneous motility and of amphetamine-induced stereotypes at 3 mg/kg Anorexiant action at 3 mg/kg | 5 | $\leq 3$ | $< 30$ | Hypertension at 1–5 mg/kg, with substantial increase of the femoral rate of flow<br>Contraction of the isolated vein<br>0 on the isolated artery |

The compounds of the formula (I) and their salts of the formula (II) are useful as stimulants of the sympathetic nervous system, as regulators of the general vascular system and particularly of the cerebral vascular system, as analgesic and anti-inflammatory agents and also as anti-ulcer agents.

In this respect, the compound described in Example 3 appears to be particularly useful and does not exhibit noteworthy toxicity at the active dosages.

The compounds are administrable to man by the oral route, or by the rectal route, in base or salt form (as tablets, capsules, drops or suppositories), or by the parenteral route, as aqueous solutions of a watersoluble salt. These various formulations may contain 50–500 mg active ingredient per unit dose. The daily dosage regimen in adults may vary from 50 mg to 2 g, depending on the therapeutic applications contemplated.

Having now described our invention what We claim as new and desire to secure by Letters Patent is:

1. A compound selected from the group consisting of compounds of the formula:

$$R'-NH-CH \begin{array}{c} (CH_2)_m \\ \\ (CH_2)_n \end{array} \!\!\! = \!\!\! \begin{array}{c} S \\ \\ N \end{array} \!\!\! \rangle \!\! -R \qquad (I)$$

and their pharmaceutically acceptable acid addition salts of the formula:

$$R'-\overset{+}{NH_2}-CH \begin{array}{c} (CH_2)_m \\ \\ (CH_2)_n \end{array} \!\!\! = \!\!\! \begin{array}{c} S \\ \\ N \end{array} \!\!\! \rangle \!\! -R \qquad (II)$$
$$X^-$$

in which:
R is selected from hydrogen and C$_{1-4}$ alkyl,
R' is selected from hydrogen and C$_{1-4}$ alkyl,
m is selected from 0, 1, 2 and 3;
n is selected from 3, 2, 1 and 0,
the sum m+n being always equal to 3, and
X$^-$ represents an anion formed by a pharmaceutically acceptable acid.

2. 6-Methylamino-4,5,6,7-tetrahydro-benzo[d]-thiazole and a pharmaceutically acceptable acid addition salt thereof.

3. A therapeutic composition useful as stimulant of the sympathetic nervous system containing an effective amount of a compound selected from the group consisting of compounds of the formula:

$$R'-NH-CH \begin{array}{c} (CH_2)_m \\ \\ (CH_2)_n \end{array} \!\!\! = \!\!\! \begin{array}{c} S \\ \\ N \end{array} \!\!\! \rangle \!\! -R \qquad (I)$$

and their pharmaceutically acceptable acid addition salts of the formula:

$$R'-\overset{+}{NH_2}-CH \begin{array}{c} (CH_2)_m \\ \\ (CH_2)_n \end{array} \!\!\! = \!\!\! \begin{array}{c} S \\ \\ N \end{array} \!\!\! \rangle \!\! -R \qquad (II)$$
$$X^-$$

in which:
R is selected from hydrogen and C$_{1-4}$ alkyl,
R' is selected from hydrogen and C$_{1-4}$ alkyl,
m is selected from 0, 1, 2 and 3,
n is selected from 3, 2, 1 and 0,
the sum m+n being always equal to 3, and
X$^-$ represents an anion formed by a pharmaceutically acceptable acid, and a therapeutically acceptable excipient.

4. Therapeutic composition as claimed in claim 3, formulated for oral, rectal or parenteral administration.

5. Therapeutic composition as claimed in claim 4, in unit dosage form, each unit dose containing 50–500 mg active ingredient.

* * * * *